United States Patent [19]
Winterfeldt et al.

[11] Patent Number: 5,336,818
[45] Date of Patent: Aug. 9, 1994

[54] PROCESS FOR THE PREPARATION OF SUBSTANTIALLY FLUORINATED ALKYL BROMIDES

[75] Inventors: Andreas Winterfeldt, Barsinghausen; Günter Bartels, Gro{burgwedel; Reinhard Knieps, Hanover, all of Fed. Rep. of Germany

[73] Assignee: Riedel-de Haen Aktiengesellschaft, Seelze, Fed. Rep. of Germany

[21] Appl. No.: 971,820

[22] PCT Filed: Aug. 8, 1991

[86] PCT No.: PCT/EP91/01502
§ 371 Date: Feb. 16, 1993
§ 102(e) Date: Feb. 16, 1993

[87] PCT Pub. No.: WO92/04307
PCT Pub. Date: Mar. 19, 1992

[30] Foreign Application Priority Data

Sep. 1, 1990 [DE] Fed. Rep. of Germany ....... 4027766

[51] Int. Cl.$^5$ .................... C07C 17/20; C07C 19/08
[52] U.S. Cl. .................... 570/170; 570/163
[58] Field of Search ................ 570/163, 170

[56] References Cited
FOREIGN PATENT DOCUMENTS 515258 11/1992 European Pat. Off. ........... 510/170
4116361 1/1992 Fed. Rep. of Germany ...... 570/170

*Primary Examiner*—Alan Siegel
*Attorney, Agent, or Firm*—Connolly and Hutz

[57] ABSTRACT

According to the process according to the invention, substantially fluorinated alkyl bromides, preferably perfluoroalkyl bromides, are prepared by reaction of substantially fluorinated alkyl iodides with organic bromine compounds in which the bromine atom is bound covalently to a carbon atom or a nitrogen atom.

19 Claims, No Drawings

PROCESS FOR THE PREPARATION OF SUBSTANTIALLY FLUORINATED ALKYL BROMIDES

The present invention relates to a process for the preparation of substantially fluorinated alkyl bromides, in particular of perfluoroalkyl bromides, starting from substantially fluorinated alkyl iodides, in particular from perfluoroalkyl iodides.

Substantially fluorinated alkyl bromides, in particular perfluoroalkyl bromides are used, for example, as intermediates for the preparation of polymer liquids, resins and elastomers, as X-ray contrast medium, for the preparation of pharmaceutical preparations and in aqueous emulsion as a blood substitute. A perfluoroalkyl bromide which is preferred as blood substitute is perfluorooctyl bromide.

A series of processes are already known for the preparation of perfluoroalkyl bromides. Thus, for example, according to Japanese Patent JP 60 184 033 (C.A. Vol. 104 (1986), 88106p) perfluoroalkyl iodides are reacted in the presence of free radical initiators with elemental bromine to give perfluoroalkyl bromide. Hazeldine (J. Chem. Soc. 1953, 3761–3768) describes on page 3763 and 3766 the reaction of perfluoroalkyl iodides with elemental bromine and with irradiation using UV light. Both methods have considerable problems associated with them in terms of materials and safety precautions, due to the use of elemental bromine, the release of elemental iodine, interhalogen compounds and hydrogen fluoride.

Examples of further preparation processes for perfluoroalkyl bromides are ($R_F$=perfluoroalkyl): reaction of bromine with compounds $R_F$—$SF_5$ at 500° C. in the presence of nickel (U.S. Pat. No. 3,456,024); reaction of bromine with compounds $R_F$—$SO_2Na$ in the presence of $KI/I_2$ (C.A., Vol. 107 (1987), 236043); reaction of bromine with salts of perfluorinated carboxylic acids (U.S. Pat. No. 2,678,953), in particular with $R_F$COOAg (U.S. Pat. No. 2,678,953) and Hauptschein et. al., J. Am. Chem. Soc. 74 (1952), 1347ff); reaction of bromine with compounds $R_F$H with simultaneous irradia-tion using UV light (J. Chem. Soc. 1953, 3761). In all these processes, the use of elemental bromine leads to significant problems in terms of materials and safety precautions. Moreover, the starting compounds are difficult to obtain or have to be prepared from the corresponding perfluoroalkyl iodides via an additional process step. This is also true of the preparation of perfluoroalkyl bromides by reaction of $R_F$$SO_3$Cl with HBr gas in the presence of a catalyst at 125° C. (EP-A1-0,298,870).

According to Fainberg et. al. JACS 79. 4172 (1957), perfluoroallyl bromide can be prepared by reaction of perfluoroallyl iodide with lithium bromide in acetone. Applying this transhalogenation to other perfluoroalkyl iodides is obvious but unsuccessful, since in normal perfluoroalkyl iodides there is no activation of iodine by an allyl group. As can be seen from Comparative Example 1 which follows, the reaction conditions described by Fainberg et. al. cannot be applied successfully to perfluorooctyl iodide. Comparative Example 2 which follows shows that the attempt of accelerating the reaction by phase transfer catalysis does not lead to a satisfactory result either.

The result of the comparative examples is as expected, since it is known that fluorine atoms considerably reduce the reactivity of alkyl halides in nucleophilic substitution reactions (cf., for example, Houben-Weyl, Methoden der organischen Chemie (Methods of Organic Chemistry), 4th Edition, Vol. 5/4, p. 685, 688).

The previously known processes for preparing substantially fluorinated alkyl bromides, in particular perfluoroalkyl bromides, are not satisfactory for the above-mentioned reasons. Accordingly, the object of the present invention is to provide a technically simple process for preparing substantially fluorinated alkyl bromides, in particular perfluoroalkyl bromides, starting from the easily accessible substantially fluorinated alkyl iodides, in particular perfluoroalkyl iodides.

This object is achieved by a process for preparing substantially fluorinated alkyl bromides, starting from substantially fluorinated alkyl iodides, characterised in that a substantially fluorinated alkyl iodide is reacted with an organic bromine compound in which the bromine atom is bound covalently to a carbon atom or a nitrogen atom.

The term "substantially fluorinated" means that in the alkyl bromides or alkyl iodides predominantly fluorine atoms and only one or a few hydrogen atoms, preferably no hydrogen atom, are present apart from the bromine atom or iodine atom. The process according to the invention is suitable in particular for preparing substantially fluorinated alkyl bromides of the formula I $$X-C_nF_{2n}-Br \qquad (I)$$

in which X is H, F or $(F_3C)_2CF$— and n is 1 to 20, preferably 4 to 6 and particularly preferably 6 to 12. In formula I, the group —$C_nF_{2n}$— has in particular the form $$-(CF_2)_n- \qquad (II)$$

To prepare a substantially fluorinated alkyl bromide by the process according to the invention, a substantially fluorinated alkyl iodide is used. This is understood to mean a compound which differs from the desired final product only by the exchange of iodine for bromine. Accordingly, in the process according to the invention, the starting materials preferably used are compounds of the formula III $$X-C_nF_{2n}-I \qquad (III)$$

in which X, n and $C_nF_{2n}$ have the already mentioned meaning.

In formulae I and III, X is preferably $(F_3C)_2$—CF— and particularly preferably F. Accordingly, the process according to the invention is suitable in particular for preparing perfluoroalkyl bromides, particularly preferably those having 6 to 12 C atoms, very particularly preferably for preparing perfluorooctyl bromide. This means that a very particularly preferred starting compound is perfluorooctyl iodide.

The substantially fluorinated alkyl iodides used as starting materials, in particular the compounds of the formula III, are known and/or can be prepared by various processes known for this class of compounds.

Organic bromine compounds in which the bromine atom is bound covalently to a carbon atom or a nitrogen atom are, for example, alkyl bromides, preferably highly brominated alkyl bromides, in particular those having 1 to 6 carbon atoms; aryl bromides, in particular phenyl bromides; acid bromides, in particular those of alkylcarboxylic acids having 1 to 6 carbon atoms or of phenylcarboxylic acids; N-brominated amides, in particular those of alkoxycarboxylic acids having 1 to 6 carbon atoms or of phenylcarboxylic acids.

When a suitable organic bromine compound is selected, it is advantageous to take its boiling point into account, in order to reach a reaction temperature in the reaction mixture which is sufficiently high for the particular synthesis.

Moreover, those organic bromine compounds which have very few or better no carbon-hydrogen bonds which can easily be eliminated by free radicals are particularly advantageous, since these can lead to undesirable side reactions, such as, for example, the reduction of the perfluoroalkyl iodide used.

Preferred organic bromine compounds are bromoform, dibromomethane, N-bromosuccinimide, benzoyl bromide, 2-bromoisobutyryl bromide and bromofluorobenzoyl bromide. Tetrabromomethane is particularly preferred.

The organic bromine compounds mentioned are known and/or can be prepared by various processes known for this class of compound.

The reaction according to the invention is carried out by simply mixing the substantially fluorinated alkyl iodide with the organic bromine compound and, if desired heating the mixture. The addition of a solvent is not required. However, the reaction can also be carried out in a suitable solvent or solvent mixture.

The amount of organic bromine compounds used per mole of substantially fluorinated alkyl iodide is such that sufficient conversion is obtained. Preferably, 0.4 to 4 mol, preferably 0.5 to 2 mol, of organic bromine compound are used per mole of substantially fluorinated alkyl iodide.

It is also possible to use more than 4 mol of organic bromine compound per mole of substantially fluorinated alkyl iodide. However, this does not bring any advantages. If the amounts of organic bromine are too small, only insufficient conversion is obtained.

The reaction temperature is preferably between 0° C. and the boiling point of the reaction mixture under atmospheric pressure. The reaction is carried out in particular at a temperature of 20° C. to the boiling point of the reaction mixture under atmospheric pressure, preferably up to the boiling point of the substantially fluorinated alkyl iodide under atmospheric pressure. In many cases, the reaction is carried out at temperatures of 50° to 160° C. The reaction rate is, as is usual, greater at higher temperatures than at lower temperatures.

It may be advantageous to carry out the reaction under an inert gas atmosphere, for example under argon.

If it is desired to use a solvent or solvent mixture, any inert solvent Which allows a sufficiently high reaction temperature is suitable. Preferred solvents are fluorobenzene, dibromofluorobenzene, nitrobenzene and biphenyl.

The reaction and work-up can take place in different ways and, for example, be carried out such that substantially fluorinated alkyl bromide formed is distilled off during the reaction or after the reaction. The work-up can also preferably be carried out such that after the reaction, the temperature of the reaction mixture is, if desired, lowered and water is added to the reaction mixture, i.e. the reaction mixture is mixed, and the resulting phases are then separated, followed by separation into their components by distillation, i.e. in particular into substantially fluorinated alkyl bromide and unconverted substantially fluorinated alkyl iodide and organic bromine compounds. The starting materials recovered in this work-up can again be added to the reaction.

In the process according to the invention, the desired substantially fluorinated alkyl bromides, preferably perfluoroalkyl bromides, are obtained in yields of up to more than 90% (relative to converted starting material). The unconverted starting materials can be recovered in a similar manner and used again.

The purities of the final products determined by gas chromatography are high and in many cases above 99%.

The invention is further illustrated by means of the examples below:

EXAMPLE 1

640 g of perfluorooctyl iodide (1.17 mole), 776 g of tetrabromomethane (2.35 mole) in 520 g of dibromofluorobenzene are stirred under reflux for 72 hours. The mixture is allowed to cool to 80° C., 2 g of sodium sulphite in 100 g of water are added, and the mixture is stirred at 60° C. for 30 minutes. The phases of the resulting 3-phase system are then separated. The bottom layer containing dibromofluorobenzene/tetrahalogenomethane can be reused after steam distillation.

The middle layer containing perfluorooctyl iodide/perfluorooctyl bromide is extracted twice with 100 g of acetic acid and then subjected to fractional distillation. The aqueous top layer is discarded.

Yield: 260 g of PFOB, which corresponds to 91%, relative to converted PFOI. 330 g PFOI (is reused).

Content (GC): greater than 99%

B.p.: 142°–143° C.

EXAMPLE 2

20 g of perfluorooctyl iodide (36.6 mmol) and 20.7 g of 3-bromo-4-fluorobenzoyl bromide (73.3 mmol) are stirred at 150° C. for 24 hours. After cooling to 40° C., 100 g of water are added as well as 10 g of $Na_2CO_3$ and 1 g of sodium sulphite. After phase separation, the organic phase is subjected to fractional distillation.

Yield: 3 g of PFOB, which corresponds to 81%, relative to converted PFOI. 16 g of PFOI (is reused).

Content: greater than 99%

B.p.: 142°–143° C.

EXAMPLE 3

640 g of perfluorooctyl iodide (1.17 mole), 776 g of tetrabromomethane (2.35 mole) in 400 g of fluorobenzene are heated to reflux. "Flourobenzene" is distilled off through a 30 cm Vigreux column up to a bottom temperature of 150° C. At a bottom temperature of 150° C., the mixture is boiled for 72 hours with stirring. After the end of the reaction, the mixture is allowed to cool to 70° C. and the "fluorobenzene" initially distilled off is readded. 200 g of sodium disulphite in 500 g of water are then metered in with stirring and the mixture is then stirred at room temperature for 30 minutes.

The phases of the resulting 3-phase system are then separated.

The bottom layer containing fluorobenzene/tetrahalomethane can be reused after regeneration.

The middle layer containing PFOI/PFOB is extracted twice with 100 g of formic acid, washed with water and then subjected to fractional distillation.

The aqueous top layer is discarded.

Yield: 215 g of PFOB, which corresponds to 88%, relative to converted PFOI. 373 g of PFOI (is reused),
Content (GC): greater than 99%
B.p.: 142°–143° C.

EXAMPLE 4

20 g of PFOI (36.6 mmol) and 16.9 g of bromoisobutyryl bromide (73.3 mmol) are refluxed at a bottom temperature of initially 150° C. for 72 hours. After cooling to 40° C., 100 g of water are added as well as 10 g of $Na_2CO_3$ and 1 g of sodium sulphite. After phase separation, the organic phase is subjected to fractional distillation.

Yield: 3 g of PFOB, which corresponds to 81% based on converted PFOI. 16 g of PFOI (is reused),
Content (GC): greater than 99%
B.p.: 192°–193° C.

EXAMPLE 5

50 g of PFOI (91.6 mmol), 16.3 g (91.6 mmol) of N-bromosuccinimide are stirred at 120° C. in 100 g of dibromofluorobenzene for 24 hours. After cooling to 70° C., 5 g of sodium disulphite in 50 g of water are added dropwise. After phase separation, the isolated PFOB/PFOI phase is washed with water and subjected to fractional distillation.

Yield: 4 g of PFOB, which corresponds to 48%, relative to converted PFOI, 41 g of PFOI (is reused).

COMPARATIVE EXAMPLE 1

100 g of perfluorooctyl iodide (183 mmol) are added to a solution of 19 g of LiBr (220 mmol) in 150 ml of dry acetone over a period of 10 minutes, and the mixture is then refluxed for 8 hours. It is poured into 500 ml of water, the organic phase is separated off and dried with a small amount of $CaCl_2$.

Yield: 100 g of perfluorooctyl iodide 98% pure. Perfluorooctyl bromide cannot be detected by gas chromatography.

COMPARATIVE EXAMPLE 2

100 g of perfluorooctyl iodide (183 mmol), 75 g of $CaBr_2$ (375 mmol), 25 ml of water and 1 g of tetrabutylammonium bromide (1.5 mol %) are refluxed for 5 hours. The mixture is poured into 500 ml of water, the organic phase is separated off, washed until free of halide and dried with a small amount of $CaCl_2$.

Yield: 94 g. GC: 1% of perfluorooctyl bromide, 96% of perfluorooctyl iodide

Analogously to Comparative Example 2, the following is obtained using 1 g of tetrabutylphosphonium bromide (1.5 mol %) as phase-transfer catalyst:

Yield: 95 g: GC: 1% of perfluorooctyl bromide. 97% of perfluorooctyl iodide.

We claim:

1. Process for the preparation of substantially fluorinated alkyl bromides, starting from substantially fluorinated alkyl iodides, comprising reacting a substantially fluorinated alkyl iodide with an organic bromine compound selected from an alkyl bromide, aryl bromine, acid bromide or an N-brominated amide wherein the fluorinated alkyl bromides differ from the fluorinated alkyl iodides only by the halo moiety being replaced.

2. Process according to claim 1, wherein the substantially fluorinated alkyl bromide product is $$X-C_nF_{2n}-Br \qquad (I)$$

in which X is H, F or $(F_3C)_2CF-$ and n is 1 to 20, and is produced from a compound of the formula $$X-C_nF_{2n}-I \qquad (III)$$

is used as substantially fluorinated alkyl iodide.

3. Process according to claim 2, wherein in formulae I and III the group $-C_nF_{2n}-$ has the form $-(CF_2)_n-$ or X has the meaning $(F_3C)_2CF-$.

4. Process according to claim 1, wherein perfluorooctyl iodide is used as substantially fluorinated alkyl iodide.

5. Process according to claim 1, wherein tetrabromomethane is used as organic bromine compound.

6. Process according to claim 1, wherein the substantially fluorinated alkyl iodide and the organic bromine compound are used in a molar ratio of 1:(0.4 to 4).

7. Process according to claim 1, wherein the reaction is carried out at temperature of 0° C. up to the boiling point of the reaction mixture.

8. Process according to claim 1, wherein after the reaction is complete the reaction mixture is mixed with water and the mixture is then separated into the phases formed and these are then separated into their components by distillation.

9. Process according to claim 8, wherein after the distillation is completed, one of said components which is recovered is the substantially fluorinated alkyl iodide which is again used as starting material.

10. The process according to claim 2, wherein n is 4 to 16.

11. The process according to claim 2, wherein n is 6 to 12 and X is F.

12. The process according to claim 2, wherein formulae I and III, the group $-C_nF_{2n}-$ has the form $-(CF_2)_n-$ and X has the meaning $(F_3C)_2CF-$.

13. The process according to claim 6, wherein the substantially fluorinated alkyl iodide and the organic bromine compound are used in a molar ratio of 1:(0.5 to 2.0).

14. The process according to claim 7, wherein reaction is carried out at a temperature of 50° to 160° C.

15. The process as claimed in claim 1, wherein said organic bromine compounds are selected from the group consisting of bromoform, dibromomethane, N-bromosuccininide, benzoyl bromide, 2-bromoisobutyl bromide, bromofluorobenzoyl bromide and tetrabromomethane.

16. The process as claimed in claim 1, wherein said fluorinated alkyl iodide is perfluorooctyl iodide.

17. The process according to claim 16, wherein the reaction is carried out at a temperature of 20° C. up to the boiling point of the reaction mixture under atmospheric pressure.

18. A process for the preparation of substantially fluorinated alkyl bromides, starting from substantially fluorinated alkyl iodides, comprising reacting a substantially fluorinated alkyl iodide with an organic bromine compound in which the bromine atom is bound covalently to a carbon atom or a nitrogen atom wherein the fluorinated alkyl bromides differ from the fluorinated alkyl iodides only by the halo moiety being replaced, wherein the substantially fluorinated alkyl iodide and the organic bromine compound are used in a molar ratio of 1:(0.4 to 4.0) and the reaction is carried out at a temperature of 0° C. up to the boiling point of the reaction mixture under atmospheric pressure, and wherein said organic bromine compounds are selected from the group consisting of bromoform, dibromomethane, N-bromosuccinimide, benzoyl bromide, 2-bromoisobutyl bromide, bromofluorobenzoylbromide and tetrabromomethane.

19. The process according to claim 1, wherein the organic bromide compounds are selected from highly brominated alkyl bromides, phenyl bromides, alkylcarboxylic acids having 1 to 6 carbon atoms or phenylcarboxylic acids.

* * * * *